United States Patent [19]

Philippe et al.

[11] Patent Number: 5,019,567
[45] Date of Patent: May 28, 1991

[54] BENZOYL PEROXIDE—QUATERNARY AMMONIUM LIPOPHILIC SALICYLATE BASED PHARMACEUTICAL AND COSMETIC COMPOSITIONS AND THEIR USE ESPECIALLY IN TREATMENT OF ACNE

[75] Inventors: Michel Philippe, Antony; Michel Hocquaux; Henri Sebag, both of Paris; Irina Beck, Villepinte; Jean P. Laugier, Antony, all of France

[73] Assignee: L'Oreal, Paris, France

[21] Appl. No.: 276,155

[22] Filed: Nov. 23, 1988

[30] Foreign Application Priority Data

Nov. 24, 1987 [FR] France ................ 87 16280

[51] Int. Cl.$^5$ .................. A61K 31/605; A61K 31/14
[52] U.S. Cl. .................... 514/164; 514/643; 514/859; 514/937; 514/944; 514/947
[58] Field of Search ............. 514/164, 643, 859, 937, 514/944, 947

[56] References Cited

U.S. PATENT DOCUMENTS 4,514,385 4/1985 Damani et al. ................ 424/81

FOREIGN PATENT DOCUMENTS

| 0029790 | 6/1981 | European Pat. Off. |
| 2340568 | 2/1974 | Fed. Rep. of Germany |
| 2328039 | 5/1977 | France |
| 2378523 | 8/1978 | France |
| 2018589 | 10/1979 | United Kingdom |
| 2150436 | 7/1985 | United Kingdom |

OTHER PUBLICATIONS

Chemical Abstracts (vol. 80:149031v) (1974).

Primary Examiner—Frederick E. Waddell
Assistant Examiner—Kevin Weddington
Attorney, Agent, or Firm—Marshall, O'Toole, Gerstein, Murray & Bicknell

[57] ABSTRACT

A pharmaceutical or cosmetic composition for topical application comprises, in a physiologically acceptable support, the combination of benzoyl peroxide and at least one quaternary ammonium lipophilic salicylate having general formula (I):

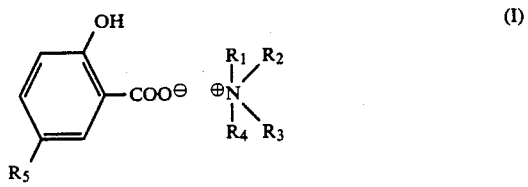

where:
(i) $R_1$, $R_2$, $R_3$ and $R_4$ may be identical or different, representing a substituted or interrupted alkyl or cycloalkyl radical;
(ii) $R_3$ and/or $R_4$ represent(s) the group:

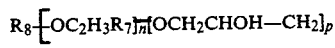

where $O \leq n \leq 4$ and p is 0 or 1; $R_8$ represents H or an alkyl, alkenyl, alkylcycloalkyl or alkylanyl radical;
(iii) $R_4$ represents an alkylenephenyl radical;
(iv), (v): $R_1$ and $R_2$ may form an aromatic or nonaromatic saturated or unsaturated heterocycle;
(vi) $R_1$, $R_2$ and $R_3$ together with nitrogen, may form polycyclic derivatives; and $R_5$ represents a group having the formula:

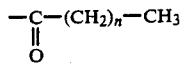

where n may vary from 0 to 10.

12 Claims, No Drawings

BENZOYL PEROXIDE—QUATERNARY AMMONIUM LIPOPHILIC SALICYLATE BASED PHARMACEUTICAL AND COSMETIC COMPOSITIONS AND THEIR USE ESPECIALLY IN TREATMENT OF ACNE

BACKGROUND OF THE INVENTION

1. Field of the Invention

The present invention concerns benzoyl peroxide quaternary ammonium lipophilic salicylate based pharmaceutical and cosmetic compositions and their use especially in treatment of acne.

The etiopathology of acne, although unclear, starts in formation of a characteristic lesion: the comedo. This produces a blockage in the pilosebaceous canal following dyskeratinization of the infundibular zone of the canal. A major effect of the blockage is to modify the rheology of the sebum and the physicochemical properties of the area. Such modification allows resident cutaneous strains to hyperproliferate which in turn triggers an inflammation reaction in the organism.

Benzoyl peroxide has been known for several years to be a particularly interesting keratolytic agent among recognized therapeutic acne treatments. In addition, it has good bacteriostatic properties.

Use of standard antibiotics in acne treatment is also widespread. They do, in fact, shown considerable bacteriostatic and anti-inflammatory activity. Orally administered active antibiotics are numerous. Among these, clindamycin and especially erythromycin show topical activity.

Antibiotics have previously been combined with benzoyl peroxide in order to increase the activity of topical antiacne compositions. In particular, erythromycin has already been combined with benzoyl peroxide (French patent FR 77 021 57).

However, a major drawback of the use of antibiotics (either alone or in combination with benzoyl peroxide) lies in their prolonged use whereupon bacterial flora become resistant, rendering the antibiotics less effective in subsequent treatment (LEYDEN, J.J; J. Am. Acad. Dermatol. 8 (1) 41–45 (1983)).

Further, benzoyl peroxide-erythromycin combinations are unstable over periods of time.

Quaternary ammonium compounds (M. GLOOR, Arch. Dermatol. Res. 265 207-212 (1979)) have been envisaged as replacements for antibiotics in topical treatment of acne. It has been shown that certain quaternary ammonium compounds are as effective as antibiotics against the main strains responsible for acne, without inducing resistance.

Combining benzoyl peroxide with quaternary ammonium compounds for topical treatment is also known (French patent FR 73 29 233). In such compositions, benzoyl peroxide acts by decomposing to liberate active oxygen in situ.

SUMMARY OF THE INVENTION

The applicants have, surprisingly, discovered that particularly effective, stable compositions can be obtained for treatment of acne, cutaneous ulcers, warts and skin dyskeratinization, also for the general treatment of dermatoses and cutaneous disorders, wherein benzoyl peroxide, combined with certain quaternary ammonium derivatives (quaternary ammonium salicylates) is stable, does not decompose and remains active.

The applicants have established that when benzoyl peroxide is combined in topical compositions with quaternary ammonium salicylates in accordance with the invention, for example in a gel, the benzoyl peroxide had not degraded and remained stable after two month's storage.

Because of the stability of the benzoyl peroxide when combined with quaternary ammonium salicylates, lower doses can be used in the compositions, thus in addition increasing cutaneous tolerance.

The applicants have also established that quaternary ammonium salicylates absorb ultraviolet radiation to a certain extent. Thus compositions according to the invention exhibit fewer of the drawbacks generally encountered with the use of benzoyl peroxide, for example instability or secondary effects.

These novel compositions are, therefore, very stable and are tolerated well. They exhibit very good antibacterial properties without producing bacterial resistance, they are keratolytic and bacteriostatic, particularly towards Propionibacterium Acnes, one of the principal acne causing germs. They are also antiseptic, bactericidal, antifungal and are active in the treatment and reduction in the number of comedos.

Because of their properties, compositions according to the invention are suitable for treatment of cutaneous disorders and dermatoses, such as acne in particular, cutaneous ulcers, warts and skin dyskeratinization.

An object of the present invention is therefore a topical pharmaceutical and cosmetic composition containing benzoyl peroxide and at least one quaternary ammonium lipophilic salicylate in an acceptable physiological support.

A further object of the invention concerns the methof of use of the composition in the therapeutic treatment of acne.

A still further object of the invention is the provision of a composition and a method of cosmetic treatment.

Further objects of the invention will become apparent from the following description and examples.

DESCRIPTION OF THE INVENTION

According to the invention, quatornary ammonium lipophilic salicylates combined with benzoyl peroxide in accordance with the invention have the following formula:

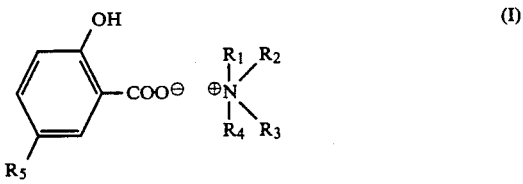

(I)

wherein:
(i) $R_1$, $R_2$, $R_3$ and $R_4$ may be identical or different and represent a linear $C_1$ to $C_{18}$ saturated alkyl radical which may contain one or more hydroxyl group(s) at the chain end or in the chain; or
(ii) $R_3$ and/or $R_4$ represent the group:

where
$0 \leq n \leq 4$ and p represents 0 or 1;
$R_8$ represents H or a $C_1$ to $C_{18}$ alkyl, alkenyl, alkylcycloalkyl or alkylanyl radical, the alkyl groups being branched or linear and where the aliphatic or aromatic cycles may have one or more $C_1$ to $C_4$ alkyl or alkoxy substitutent(s);
$R_7$ represents H, $CH_3$ or $CH_2OH$; and when $R_7$ represents $CH_2OH$, $R_8$ is then other than H and p equals 1;
Otherwise p=0.

Group $(OC_2H_3R_7)$ represents one or other of the following chains:

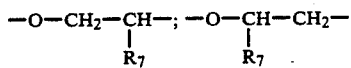

$R_1$ and $R_2$ having the meanings given in paragraph (i);

(iii) $R_4$ represents the group:

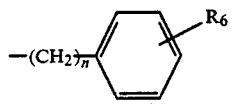

where n is 0 or 1 and $R_1$, $R_2$ and $R_3$ have the meanings given above, $R_6$ represents hydrogen, hydroxyl, halogen, an alkyl or hydroxyalkyl group, or a $C_1$ to $C_{18}$ acyl group; or (iv) $R_1$ and $R_2$ form an aromatic heterocyclo (in which case $R_3$ does not exist) conforming to the formula:

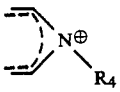

$R_4$ having the meanings given above, or (v) $R_1$ and $R_2$ form a non-aromatic, saturated or unsaturated heterocycle which may be interrupted by an oxygen atom in which case $R_4$ represents a group as defined above and $R_3$ a group as defined in (i); or (vi) $R_1$, $R_2$ and $R_3$ form a non-aromatic saturated or unsaturated bicyclic group, $R_4$ representing in this case a group as defined above; and $R_5$ represents a group having formula:

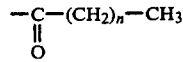

where n is an integer and varies from 0 to 16.

These compounds have been specifically described in French patent application No. 86 16 763 and are preferably prepared from a salt, such as the corresponding quaternary ammonium carbonate in particular, dissolved in an alcoholic medium, preferably methanol, to which the selected lipophilic salicylic acid derivative, also dissolved in an alcohol such as ethanol or methanol or in an other such as tetrahydrofuran, is added. The reaction begins spontaneously and its progress is followed by evolution of carbon dioxide.

The following quaternary ammonium lipophilic salicylates are particularly preferred:
hexadecyltrimethylammonium 5-octanoyl salicylate,
hexadecyltrimethylammonium 5-decanoyl salicylate,
hexadecyltrimethylammonium 5-dodecanoyl salicylate,
hexadecylpyridinium 5-octanoyl salicylate,
hexadecylpyridinium 5-decanoyl salicylate,
hexadecylpyridinium 5-dodecanoyl salicylate,
benzyldimethylhexadecylammonium 5-octanoyl salicylate,
benzyldimethylhexadecylammonium 5-decanoyl salicylate,
benzyldimethylhexadecylammonium 5-dodecanoyl salicylate,
benzyltrimethylammonium 5-decanoyl salicylate,
hexadecyldimethylhydroxyethylammonium 5-decanoyl salicylate,
tetramethylammonium 5-dodecanoyl salicylate,
dodecylethyldimethylammonium 5-decanoyl salicylate,
trimethyl -hydroxyethylammonium 5-decanoyl salicylate,
trimethyl -hydroxyethylammonium 5-dodecanoyl salicylate,
N-dodecyl, N-methylmorpholinium 5-decanoyl salicylate,
N-methyl, N-octyl piperidinium 5-dodecanoyl salicylate,
benzethonium 5-octanoyl salicylate,
benzethonium 5-dodecanoyl salicylate.

These compounds can be prepared in the manner described below:

EXAMPLES OF THE INVENTION

A

Preparation of N-hexadecyl,N,N,N-trimethylammonium 5-octanoyl salicylate 2 g (7.57 mmoles) 5-octanoyl salicylic acid dissolved is 15 ml methanol was added to a solution of 2.62 g (4.16 mmoles) hexadecyltrimethylammonium carbonate dissolved in 15 ml methanol. The mixture was stirred at ambient temperature for one hour then the solvent was evaporated off and the solid white residue was recrystallized from a mixture of acetone/diethyl ether to produce 3.8 g (91.5% yield) hexadecyltrimethyl ammonium 5-octanoyl salicylato.

Melting Pt=130° C. (acetone/diethyl ether),

| Elemental analysis: $C_{34}H_{61}NO_4$; M. Wt = 547.9 | | |
|---|---|---|
| C | H | N |
| Calculated % 74.54 | 11.22 | 2.56 |
| Found % 74.48 | 11.31 | 2.62 |

$^1H$ $^{13}C$ NMR spectra confirmed the expected structure, displaying the values characteristic of the ammonium cation and of the 5-octanoyl salicylate anion.

B

Preparation of N-hexadecyl,N,N,N-trimethylammonium 5-dodecanoyl salicylate 2 g (6.85 mmoles) 5-decanoyl salicylic acid dissolved in 15 ml ethanol was added to 2.2 g (3.5 mmoles) hexadecyltrimethylammonium carbonate dissolved in 15 ml methanol. The mixture was stirred at ambient temperature for one hour then the solvent was evaporated off and the solid white residue obtained was recrystallized from a mixture of acetone/diethyl ether to produce 3.8 g (96% yield) of hexadecyltrimethyl ammonium 5-decanoyl salicylate.

Melting Pt=130° C. (acetone/diethyl ether),

| Elemental analysis: $C_{36}H_{65}NO_4$; M. Wt = 575.9 | | | |
|---|---|---|---|
| | C | H | N |
| Calculated % | 75.08 | 11.37 | 2.43 |
| Found | 75.05 | 11.42 | 2.44 |

$^1H$ and $^{13}C$ NMR spectra confirmed the expected structure, displaying the values characteristic of the quaternary ammonium cation and the 5-decanoyl salicylate anion.

C

Preparation of N-hexadecyl,N,N,N-trimethylammonium 5-dodecanoyl salicylate 2 g (6.25 mmoles) 5-dodecanoyl salicylic acid dissolved in 15 ml ethanol was added to a solution of 2 g (3.18 mmoles) hexadecyltrimethylammonium carbonate dissolved in 15 ml methanol. The mixture was stirred at ambient temperature for one hour, then the solvent was evaporated off and the solid white residue obtained was recrystallized from a mixture of acetone/diethyl ether to produce 3.5 g (93% yield) hexadecyltrimethylammonium 5-dodecanoyl salicylate.

Melting Pt=130° C. (acetone/diethyl ether).

| Elemental analysis: $C_{38}H_{69}NO_4$; M. Wt = 604 | | | |
|---|---|---|---|
| | C | H | N |
| Calculated % | 75.57 | 11.52 | 2.32 |
| Found % | 75.17 | 11.61 | 2.5 |

A $^{13}C$ NMR spectrum confirmed the expected structure, displaying the values characteristic of the quaternary ammonium cation and 5-dodecanoyl salicylate anion.

A UV spectrum (in ethanol) exhibited an absorption peak, $\lambda_{max}=280$ nm; molar extinction coefficient $\epsilon=14080$.

D

Preparation of the monohydrate of N-hexadecylpyridinium 5-octanoyl salicylate 2 g (7.57 mmoles) 5-octanoyl salicylic acid dissolved in 15 ml methanol was added to a solution of 2.5 g (3.79 mmoles) hexadecylpyridinium carbonate dissolved in 15 ml methanol. The mixture was stirred at ambient temperature for one hour, then the crude brown residue was filtered off and the filtrate evaporated to dryness to produce 4.2 g (98% yield) hexadecylpyridinium 5-octanoyl salicylate.

| Elemental analysis: $C_{36}H_{57}NO_4$, $1H_2O$; M. Wt = 585.9 | | | |
|---|---|---|---|
| | C | H | N |
| Calculated % | 73.8 | 10.15 | 2.39 |
| Found % | 73.22 | 9.77 | 2.31 |

A $^{13}C$ NMR spectrum confirmed the expected structure, displaying values characteristic of the quaternary ammonium cation and the 5-octanoyl salicylate anion.

A UV spectrum in ethanol exhibited an absorption peak $\lambda_{max}=279$ nm; molar extinction coefficient $\epsilon=21450$.

E

Preparation of the sesquihydrate of N-hexadecylpyridinium 5-decanoyl salicylate 2 g (6.85 mmoles) 5-decanoyl salicylic acid dissolved in 15 ml ethanol was added to a solution of 2.3 g (3.44 mmoles) hexadecylpyridinium carbonate dissolved in 15 ml methanol. The mixture was stirred at ambient temperature for one hour, then the solvents were evaporated off and the brown residue obtained was recrystallized from a mixture of acetone/diethyl ether to produce 3.9 g (96% yield) hexadecylpyridinium 5-decanoyl salicylate.

Melting Pt=73° C. (acetone/diethyl ether).

| Elemental analysis: $C_{38}H_{61}NO_4$, $1,5H_2O$; M. Wt = 622.9 | | | |
|---|---|---|---|
| | C | H | N |
| Calculated % | 73.27 | 10.36 | 2.25 |
| Found % | 73.64 | 9.64 | 1.82 |

A $^{13}C$ NMR spectrum confirmed the expected structure, displaying values characteristic of the aromatic quaternary ammonium cation and of the 5-decanoyl salicylate anion.

F

Preparation of the hydrate of N-hexadecylpyridinium 5-dodecanoyl salicylate 2 g (6.25 mmole) 5-dodecanoyl salicylic acid dissolved in 15 ml ethanol was added to a solution of 2.1 g (3.14 mmoles) hexadecylpyridinium carbonate dissolved in 15 ml ethanol, the mixture was stirred at ambient temperature for one hour, then the solvents were evaporated off and the brown residue obtained was recrystallized from a mixture of acetone/diethyl ether to produce 3.7 g (95% yield) hexadecylpyridinium 5-dodecanoyl salicylate.

Melting Pt=79° C. (acetone/diethyl ether)

| Elemental analysis: $C_{40}H_{65}NO_4$, $1H_2O$; M. Wt = 642 | | | |
|---|---|---|---|
| | C | H | N |
| Calculated % | 74.84 | 10.52 | 2.18 |
| Found % | 74.61 | 10.12 | 1.96 |

A $^{13}C$ NMR spectrum confirmed the expected structure, displaying values characteristic of the aromatic quaternary ammonium cation and of the 5-dodecanoyl salicylate.

The UV spectrum (in ethanol) exhibited an absorption peak, $\lambda_{max}=279$ nm; molar coefficient of extinction $\epsilon=18910$.

G

Preparation of N-benzyl, N, N-dimethyl, N-hexadecylammonium 5-octanoyl salicylate 2 g (7.57 mmoles) 5-octanoyl salicylic acid dissolved in 15 ml methanol was added to a solution of 3 g (3.84 mmoles) benzyldimethylhexadecylammonium carbonate dissolved in 15 ml methanol. The mixture was stirred at ambient temperature for one hour, then the solvent was evaporated off and the white residue was recrystallized from a mixture of acetone/diethyl ether to produce 4.5 g (95% yield) benzyldimethylhexadecylammonium 5-octanoyl salicylate.

Melting Pt=114° C. (acetone/diethyl ether).

Elemental analysis: $C_{40}H_{65}NO_4$;
M. Wt = 623.9

|  | C | H | N |
|---|---|---|---|
| Calculated % | 77.00 | 10.50 | 2.24 |
| Found % | 77.02 | 10.58 | 2.38 |

A $^{13}C$ NMR spectrum confirmed the expected structure, displaying values characteristic of the quaternary ammonium cation and 5-octanoyl salicylate.

Compounds H to Q were prepared in analogous fashion to that described in examples A to G.

H

Preparation of N-benzyl, N, N-dimethyl, N-hexadecylammonium 5-decanoyl salicylate Melting Pt=113° C. (acetone/diethyl ether).

Elemental analysis: $C_{42}H_{69}NO_4$;
M. Wt = 652

|  | C | H | N |
|---|---|---|---|
| Calculated % | 77.37 | 10.67 | 2.15 |
| Found % | 77.22 | 10.69 | 2.25 |

I

Preparation of N-benzyl, N, N-dimethyl, N-hexadecylammonium 5-dodecanoyl salicylate Melting Pt=117° C. (acetone/diethyl ether).

Elemental analysis: $C_{44}H_{73}NO_4$;
M. Wt = 680.88

|  | C | H | N |
|---|---|---|---|
| Calculated % | 77.71 | 10.82 | 2.06 |
| Found % | 77.15 | 10.81 | 2.08 |

The UV spectrum (in ethanol) exhibited an absorption peak $\lambda_{max}=281$ nm; molar coefficient of extinction $\epsilon=17720$.

J

Preparation of N-benzyl, N,N,N-trimethylammonium 5-decanoyl salicylate

Melting Pt=135° C. (acetone/diethyl ether)

Elemental analysis: $C_{27}H_{39}NO_4$;
M. Wt = 441.6

|  | C | H | N |
|---|---|---|---|
| Calculated % | 73.43 | 8.9 | 3.17 |
| Found % | 73.01 | 8.74 | 3.18 |

K

Preparation of N, N-dimethyl, N, β-hydroxyethylammonium 5-decanoyl salicylate

Elemental analysis: $C_{37}H_{68}NO_5$, ½$H_2O$
M. Wt = 615.96

|  | C | H | N |
|---|---|---|---|
| Calculated % | 72.15 | 11.29 | 2.12 |
| Found % | 72.51 | 10.85 | 2.27 |

L

Preparation of N,N,N,N-tetramethylammonium 5-dodecanoyl salicylate

Melting Pt=97° C. (acetone/diethyl ether).

Elemental analysis: $C_{23}H_{40}NO_4$;
M. Wt = 390.15

|  | C | H | N |
|---|---|---|---|
| Calculated % | 70.8 | 10.33 | 3.59 |
| Found % | 70.27 | 9.87 | 3.38 |

M

Preparation of trimethyl-β-hydroxyethylammonium 5-dodecanoyl salicylate

Melting Pt=67° C. (methanol/diethyl ether).

Elemental analysis: $C_{24}H_{41}NO_5$;
M. Wt = 423.6

|  | C | H | N |
|---|---|---|---|
| Calculated % | 68.05 | 9.76 | 3.31 |
| Found % | 68.09 | 9.59 | 2.69 |

UV spectrum (ethanol): $\lambda_{max}=280$ nm; $\lambda=16,640$.

N

Preparation of trimethyl-β-hydroxyethylammonium 5-decanoyl salicylate

Elemental analysis: $C_{22}H_{35}NO_5$, ¾$H_2O$;
M. Wt = 407.6

|  | C | H | N |
|---|---|---|---|
| Calculated % | 64.82 | 9.51 | 3.43 |
| Found % | 64.75 | 9.36 | 3.01 |

O

Preparation of dimethylethyldodecylammonium 5-decanoyl salicylate

Melting Pt=65° C. (acetone/diethyl ether).

Elemental analysis: $C_{33}H_{59}NO_4$, $H_2O$;
M. Wt = 551.9

|  | C | H | N |
|---|---|---|---|
| Calculated % | 71.8 | 11.14 | 2.62 |
| Found % | 72.07 | 10.74 | 2.33 |

P

Preparation of N-methyl, N-octylpiperidinium 5-dodecanoyl salicylate

Melting Pt = 45° C. (acetone/diethyl ether).

| Elemental analysis: $C_{33}H_{57}NO_4$, 0.5 $H_2O$; M. Wt = 540.9 | | | |
|---|---|---|---|
| | C | H | N |
| Calculated % | 73.28 | 10.81 | 2.59 |
| Found % | 73.31 | 11.02 | 2.7 |

Q

Preparation of N-dodecyl, N-methyl morpholinium 5-decanoyl salicylate

Melting Pt = 78° C. (acetone/diethyl ether).

| Elemental analysis: $C_{34}H_{59}NO_5$; M. Wt = 561.8 | | | |
|---|---|---|---|
| | C | H | N |
| Calculated % | 72.68 | 10.58 | 2.49 |
| Found % | 72.58 | 10.68 | 2.6 |

R

Preparation of benzethonium 5-octanoyl salicylate 2.2 g (8.4 mmoles) 5-octanoyl salicylic acid dissolved in 100 ml methanol was added to a solution of 3.7 g (4.2 mmoles) benzethonium carbonate dissolved in 100 ml methanol. The mixture was stirred at ambient temperature for one hour, then the solution was filtered and the filtrate evaporated to dryness to produce 5.5 g (98% yield) benzethonium 5-octanoyl salicylate.

| Elemental analysis: $C_{42}H_{61}NO_6$, 2$H_2O$; M. Wt = 712 | | | |
|---|---|---|---|
| | C | H | N |
| Calculated % | 70.85 | 9.20 | 1.97 |
| Found % | 70.93 | 9.07 | 2.07 |

A $^{13}C$ NMR spectrum confirmed the expected structure, displaying values characteristic of the quaternary ammonium cation and 5-octanoyl salicylate anion.

S

Preparation of benzethonium 5-dodecanoyl salicylate 2 g (6.4 mmoles) 5-dodecanoyl salicylic acid dissolved in 100 ml ethanol was added to a solution of 2.82 g (3.2 mmoles) benzethonium carbonate dissolved in 100 ml methanol. The mixture was stirred at ambient temperature for one hour, then the solution was filtered and the filtrate evaporated to dryness to produce 4.5 g (97% yield) benzethonium 5-dodecanoyl salicylate.

| Elemental analysis: $C_{46}H_{69}NO_6$, $H_2O$; M. Wt = 750 | | | |
|---|---|---|---|
| | C | H | N |
| Calculated % | 73.66 | 9.54 | 1.87 |
| Found % | 73.60 | 9.48 | 1.85 |

A $^{13}C$ NMR spectrum confirmed the expected structure, displaying values characteristic of the quaternary ammonium cation and 5-dodecanoyl salicylate anion.

Pharmaceutical or cosmetic compositions according to the invention are primarily characterized in that they are topical compositions containing in combination and in a physiologically acceptable support benzoyl peroxide and at least one quaternary ammonium lipophilic salicylate corresponding to general formula (I) given above.

The compositions may be in the form of solutions, emulsions, suspensions, gels or dispersions, containing at least one compound corresponding to formula (I) in concentrations of between 0.01 and 25% by weight with respect to the total composition weight, preferably between 0.1 and 3% by weight, and benzoyl peroxide in concentrations of between 0.1 and 20% by weight with respect to the total composition weight, preferably between 1 and 10% by weight.

These compositions may contain other well known physiologically acceptable media and additives. Solutions, micro-suspensions or vesicular emulsions, for example, may be prepared using one or more physiologically acceptable organic solvent(s) selected in addition to water from the following examples: acetone, ethanol, isopropyl alcohol, glycol others such as products sold under the trade name "DOWANOL", polyglycols, polyethyleneglycols, $C_1$ to $C_4$ alkyl esters of short-chain acids, preferably ethyl or isopropyl laclates, fatty acid triglycerides such as products sold under the trade name "MIGLYOL" and isopropyl myristate.

Compositions according to the invention may also include thickening and gelling agents selected from the following examples: cellulose and its derivatives, guar gum, heterobiopolysaccharides, reticulated polyacrylic acid, methacrylic acid/methyl methacrylate copolymer, poly-$\beta$-alanine, colloidal silica, softenors, superfatting agents, emollients, moisturizers, surfactants, pH regulators, penetrating agents, preservatives, antifoaming agents, solar filters, oils, waxes, perfumes, dyes and/or pigments intended to color either the skin or the composition itself, and any other ingredient in normal use in topical application compositions.

Vehicles and ingredients which could react undesirably with the benzoyl peroxide must, of course, be omitted.

Compositions according to the invention may also contain, in combination, antiacne agents such as retinoic derivatives, antibacterial agents, anti-inflammatory agents, non-hormonal steroidal compounds, in particular pregnenolone, and/or keratolytic or comedolytic agents.

Creams, milks, gels, dispersions or micro-emulsions, compositions of differing thicknesses, impregnated pads, ointments, sticks or soap tablets are examples of galenical forms which are primarily suited for topical application.

Pharmaceutical compositions according to the invention are characterized in that they contain benzoyl peroxide and at least one quaternary ammonium lipophilic salicylate having formula (I) in a pharmaceutically acceptable support.

Such pharmaceutical compositions, in particular because of their antibacterial and keratolytic properties, may be used as a medicament in the therapeutic treatment of dermatoses, particularly acne.

A further object of the invention, therefore, is constituted by the use of pharmaceutical compositions in the preparation of a medicament for the treatment of dermatoses, in particular acne, cutaneous ulcers, warts and skin dyskeratinisation.

Therapeutic treatment of acne consists in applying the composition defined above to the affected areas, two or three times a day for three to 25 weeks depending on the severity of the case.

Cosmetic compositions which constitute a still further object of the invention are characterized in that they contain benzoyl peroxide and at least one quaternary ammonium lipophilic salicylate having formula (I) in a cosmetically acceptable support.

Cosmetic compositions according to the invention may be used for cosmetic skin treatment particularly in keratolytic treatment, or treatment against spots or warts.

A still further object of the invention concerns a cosmetic treatment procedure consisting in applying a composition according to the invention to the skin in order to cleanse or purify it.

The following examples are intended to illustrate the invention without in any way limiting its scope.

The following compositions were prepared:

EXAMPLE 1

| | |
|---|---|
| Benzoyl peroxide, 100% active | 5.0 g |
| Hexadecyltrimethylammonium 5-octanoyl salicylate | 1.0 g |
| Diethyleneglycol, monoethylether | 20.0 g |
| Ethanol, 90° | 50.0 g |
| Hydroxyethyl cellulose | 2.0 g |
| Distilled water | qsp 100.0 g |

The composition was in the form of a gel.

EXAMPLE 2

| | |
|---|---|
| Benzoyl peroxide, 100% active | 10.0 g |
| Hexadocyltrimethylammonium 5-dodecanoyl salicylate | 0.5 g |
| Propyleneglycol | 10.0 g |
| Ethanol | 40.0 g |
| Hydroxyethyl cellulose | 2.2 g |
| Colloidal silica | 2.0 g |
| Propyleneglycol, monoethylether | 15.0 g |
| Distilled water | qsp 100.0 g |

The composition was in the form of a gel.

EXAMPLE 3

| | |
|---|---|
| Benzoyl peroxide, 100% active | 5.0 g |
| Hexadecltrimethylammonium 5-decanoyl salicylate | 1.0 g |
| Polyethylglycol stearate, oxyethylenated to 50 moles ethylene oxide | 4.2 g |
| Glycerol, monostearate | 1.1 g |
| Cetyl alcohol | 2.0 g |
| Stearyl alcohol | 17.0 g |
| Hydroxyethyl cellulose | 0.35 g |
| Distilled water | qsp 100.0 g |

The composition was in the form of a cream.

EXAMPLE 4

| | |
|---|---|
| Benzoyl peroxide, 100% active | 10.0 g |
| Hexadecyltrimethylammonium 5-dodecanoyl salicylate | 0.5 g |
| PEG 75 stearate (polyethylene glycol | 14.0 g |

-continued

| | |
|---|---|
| oxyethylenated to 75 moles ethylene oxide + glycol monostearate, sold by GATTEFOSSE under the trade name GELOT 64) | |
| MIGLYOL 812 ($C_6$-$C_{12}$ fatty acid triglycerides, sold by DYNAMIT NOBEL) | 17.0 g |
| Cetyl alcohol | 2.0 g |
| Stearyl alcohol | 2.0 g |
| Hydroxypropyl guar | 0.3 g |
| Distilled water | qsp 100.0 g |

The composition was in the form of a gel.

EXAMPLE 5

| | |
|---|---|
| Benzoyl peroxide, 100% active | 2.5 g |
| Hexadecyltrimethylammonium 5-octanoyl salicylate | 1.0 g |
| Diethyleneglycol, monoethylether | 20.0 g |
| Ethanol, 90% | 50.0 g |
| Hydroxyethyl cellulose | 2.0 g |
| Distilled water | qsp 100.0 g |

The composition was in the form of a gel.

On weekly application of compositions according to examples one to five to skin susceptible to acne, it could be seen that, after three to six weeks the skin cleared up, becoming noticeably less greasy and having a reduced number of comedos.

We claim:

1. A pharmacoutical or cosmetic composition for topical application comprising in combination, in a physiologically aceptable support, benzoyl peroxide and at least one quaternary ammonium lipophilic salicylate having general formula (I):

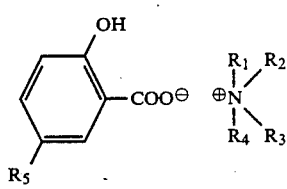

wherein:
(i) $R_1$, $R_2$, $R_3$ and $R_4$ may be identical or different and represent a linear $C_1$ to $C_{18}$ saturated alkyl radical which may contain one or more hydroxyl group(s) at the chain end or in the chain; or
(ii) $R_3$ and/or $R_4$ represent the group:

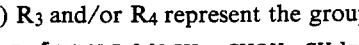

where
$0 \leq n \leq 4$ and p represents 0 or 1;
$R_8$ represents H or a $C_1$ to $C_{18}$ alkyl, alkenyl, alkylcycloalkyl or alkylaryl radical, the alkyl groups being branched or linear and where the aliphatic or aromatic cycles may have one or more $C_1$ to $C_4$ alkyl or alkoxy substitutent(s);
$R_7$ represents H, $CH_3$ or $CH_2OH$; and when $R_7$ represents $CH_2OH$, $R_8$ is then other than H and p equals 1;
Otherwise p=0;
Group ($OC_2H_3R_7$) represents one or other of the following chains:

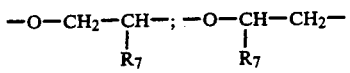

$R_1$ and $R_2$ having the meanings given in paragraph (i);

(iii) $R_4$ represents the group:

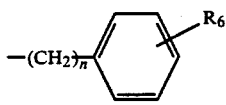

where n is 0 or 1 and $R_1$, $R_2$ and $R_3$ have the meanings given above, $R_6$ represents hydrogen, hydroxyl, halogen, an alkyl or hydroxyalkyl group, or a $C_1$ to $C_{18}$ acyl group; or (iv) $R_1$ and $R_2$ form an aromatic heterocycle (in which case $R_3$ does not exist) conforming to the formula:

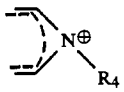

$R_4$ having the meanings given above, or (v) $R_1$ and $R_2$ form a non-aromatic, saturated or unsaturated heterocycle which may be interrupted by an oxygen atom in which case $R_4$ represents a group as defined above and $R_3$ a group as defined in (i); or (vi) $R_1$, $R_2$ and $R_3$ form a non-aromatic saturated or unsaturated bicyclic group, $R_4$ representing in this case a group as defined above; and $R_5$ represents a group having formula:

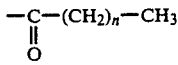

where n is an integer and varies from 0 to 16.

2. A composition according to claim 1 wherein, in formula (I) of the quaternary ammonium lipophilic salicylate, $R_4$ represents a benzyl group and $R_1$, $R_2$ and $R_3$ have the meanings given in paragraph (i) of claim 1.

3. A composition according to claim 1 characterized in that the quaternary ammonium lipophilic salicylate is selected from the following compounds: hexadecyltrimethylammonium 5-octanoyl salicylate, hexadecyltrimethylammonium 5-decanoyl salicylate, hexadecyltrimethylammonium 5-dodecanoyl salicylate, hexadecylpyridinium 5-octanoyl salicylate, hexadecylpyridinium 5-decanoyl salicylate, hexadecylpyridinium 5-dodecanoyl salicylate, hexadecyldimethylhydroxyethylammonium 5-decanoyl salicylate, tetramethylammonium 5-dodecanoyl salicylate, dodecylethyldimethylammonium 5-decanoyl salicylate, trimethyl β-hydroxyethylammonium 5-decanoyl salicylate, trimethyl β-hydroxyethylammonium 5-dodecanoyl salicylate, N-dodecyl, N-methylmorpholinium 5-decanoyl salicylate, N-methyl, N-octyl piperidinium 5-dodecanoyl salicylate, benzothonium 5-octanoyl salicylate, benzethonium 5-dodecanoyl salicylate.

4. A composition according to claim 2 characterized in that the quaternary ammonium lipophilic salicylate is selected from the following compounds: benzyldimethylhexadecyl ammonium 5-octanoyl salicylate, benzyldimethylhexadecyl ammonium 5-decanoyl salicylate, benzyldimethylhexadecyl ammonium 5-dodecanoyl salicylate, benzyltrimethylammonium 5-decanoyl salicylate.

5. A composition according to claim 1 wherein said benzoyl peroxide is present in proportions of 0.1 to 20% by weight with respect to the total composition weight.

6. A composition according to claim 1 wherein said quaternary ammonium lipophilic salicylate is present in proportions of 0.01 to 25% by weight with respect to the total composition weight.

7. A composition according to claim 5 wherein said benzoyl peroxide is present in proportions of 1 to 10% by weight with respect to the total composition weight.

8. A composition according to claim 6 wherein said quaternary ammonium lipophilic salicylate is present in proportions of 0.1 to 3% by weight with respect to the total composition weight.

9. A pharmaceutical composition according to claim 1 wherein said physiologically acceptable support is a pharmaceutically acceptable support.

10. A cosmetic composition according to claim 1 wherein said physiologically acceptable support is a cosmetically acceptable support.

11. A composition according to claim 1 in a form selected from the group consisting of a gel, a solution, a dispersion, an emulsion and a suspension.

12. A composition according to claim 1 in a form selected from the group consisting of a cream, a milk, a gel, a dispersion or microemulsion, a composition of any thickness, an impregnated pad, an ointment, a stick and a tablet of soap.

* * * * *